(12) United States Patent
Barnvos et al.

(10) Patent No.: US 8,574,653 B2
(45) Date of Patent: Nov. 5, 2013

(54) INTERMITTENT FLOW EXTRUSION PROCESS AND FOOD PRODUCT

(75) Inventors: Donald Barnvos, Huntington Beach, CA (US); Hilda Fleischman, Torrance, CA (US); Davor Juravic, San Pedro, CA (US); William Keehn, Perry, KS (US); Steven Bautista, Long Beach, CA (US); Eric J. Lew, Los Angeles, CA (US); Yomayra Diaz, Long Beach, CA (US); Franjo Baltorinic, Downey, CA (US)

(73) Assignee: Del Monte Corporation, San Francisco, CA (US)

( * ) Notice: Subject to any disclaimer, the term of this patent is extended or adjusted under 35 U.S.C. 154(b) by 722 days.

(21) Appl. No.: 11/442,549

(22) Filed: May 30, 2006

(65) Prior Publication Data
US 2008/0003338 A1 Jan. 3, 2008

Related U.S. Application Data

(60) Provisional application No. 60/685,074, filed on May 27, 2005.

(51) Int. Cl.
*A23L 1/00* (2006.01)

(52) U.S. Cl.
USPC ............ 426/516; 426/512; 426/513; 426/514; 426/518; 425/97; 425/114; 425/132; 425/133.1; 425/465

(58) Field of Classification Search
USPC ......... 426/518, 805, 512–514, 516–517, 635; 425/97, 114, 133.1, 132, 464–466
See application file for complete search history.

(56) References Cited

U.S. PATENT DOCUMENTS

| | | | |
|---|---|---|---|
| 3,422,648 A | 1/1969 | Lemelson | |
| 3,557,403 A | 1/1971 | Lemelson | |
| 3,788,922 A * | 1/1974 | Rasmussen | 156/155 |
| 4,358,468 A * | 11/1982 | Dolan et al. | 426/250 |
| 4,372,734 A | 2/1983 | Dolan et al. | |
| 4,900,572 A * | 2/1990 | Repholz et al. | 426/282 |
| 5,279,781 A | 1/1994 | Yamasaki | |
| 6,206,678 B1 | 3/2001 | Keehn et al. | |
| 6,410,079 B2 | 6/2002 | Cheuk et al. | |
| 6,669,986 B1 | 12/2003 | Mushiake et al. | |
| 6,740,349 B2 * | 5/2004 | Franklin et al. | 426/513 |

(Continued)

OTHER PUBLICATIONS

International Search Report mailed Sep. 25, 2007 for International Application No. PCT/US 2006/020751.

(Continued)

*Primary Examiner* — Drew Becker
*Assistant Examiner* — Luana Z Long
(74) *Attorney, Agent, or Firm* — Buchanan Ingersoll & Rooney PC

(57) ABSTRACT

An extrusion process incorporates a forming manifold where a tubular flow of a second material is intermittently interrupted while a core flow of a first material is discharged substantially continuously. Subsequently, the core flow is severed to form individual food items or treats for humans, animals, and the like, where the tubular flow results in an outer component surrounding an inner component which protrudes from one or both ends of the outer component. Material of the core flow is bone-like, while material of the tubular flow is meat like. Material of the tubular flow may include material from the core flow subjected to mixing in a static mixer to achieve a marbled texture of the outer material.

21 Claims, 13 Drawing Sheets

(56) References Cited

U.S. PATENT DOCUMENTS

| | | |
|---|---|---|
| 6,827,957 B2 | 12/2004 | Paluch et al. |
| 6,887,503 B1 * | 5/2005 | Rasmussen .................... 426/94 |
| 6,896,924 B2 | 5/2005 | Hernandez et al. |
| 2003/0066433 A1 | 4/2003 | Rothamel et al. |
| 2004/0052906 A1 * | 3/2004 | Hernandez et al. ............. 426/89 |
| 2007/0184142 A1 | 8/2007 | Prue |

OTHER PUBLICATIONS

International Preliminary Report on Patentability mailed Nov. 30, 2007 in International Application No. PCT/US 2006/020751.

* cited by examiner

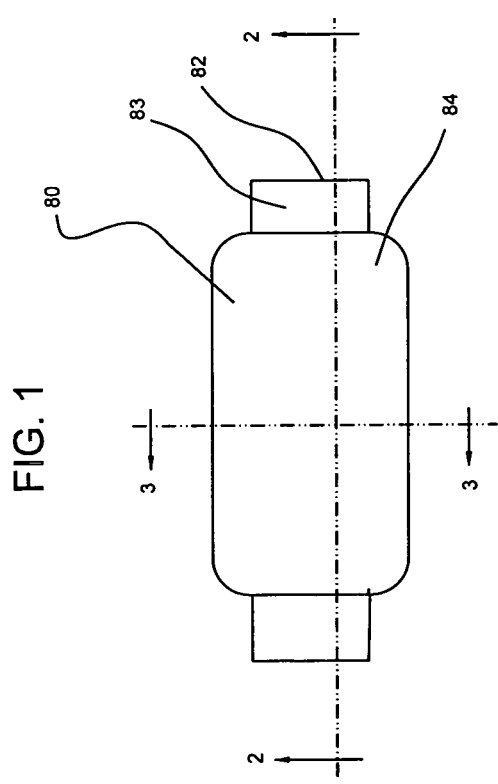

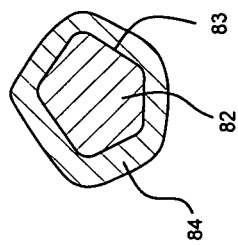
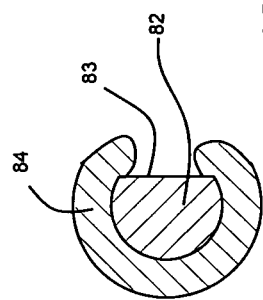
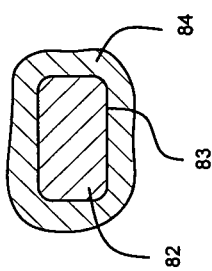

US 8,574,653 B2

INTERMITTENT FLOW EXTRUSION PROCESS AND FOOD PRODUCT

CROSS-REFERENCE TO RELATED APPLICATION

This application claims the benefit of priority to U.S. Provisional Application Ser. No. 60/685,074, filed May 27, 2005, which is incorporated herein by reference.

BACKGROUND

This invention relates generally to comestible products as well as processes for making them. In particular, the invention concerns a food product resembling a meaty morsel, as well as an intermittent flow extrusion process for making it, and forming manifolds for use in the process.

BRIEF DESCRIPTION OF THE DRAWINGS

Many objects and advantages of the present invention will be apparent to those skilled in the art when this specification is read in conjunction with the drawings wherein like reference numerals are applied to like elements and wherein:

FIG. 1 is a top view of a food product make by the process of this invention;

FIGS. 6 and 7 are transverse cross-sectional views of food products having generally polyhedral configurations;

FIG. 8 is a transverse cross-sectional view of a food product having an outer portion substantially encompassing the lateral surface of an inner portion;

DETAILED DESCRIPTION OF THE ILLUSTRATED EMBODIMENTS

In one aspect, the present invention concerns an edible food product. The edible food product may be consumed by humans, animals, or pets depending upon the recipe used, as well as whether the manufacturing facility is USDA license. A particular food product may be shaped like a beef or pork rib. For purposes of this description, the food product described may be a pet comestible or treat, such as a treat for a dog. Such treats may be used, for example, as a training aid and reward for pet behavior being encouraged. In addition, the treat can be used simply as a novelty to show affection for the pet. Other uses for the pet treat will also be apparent to those skilled in the art.

Desirable characteristics of such pet treats include the taste, texture, and palatability of the treat to the animal. Related to those characteristics is the shape of the treat. Dogs, for example, are often fond of meaty table scraps and bones. In times past, dogs were often given bones from red meat to gnaw on. More recently, however, pet owners are discouraged from giving natural bones to their pet animals.

Figure 2:
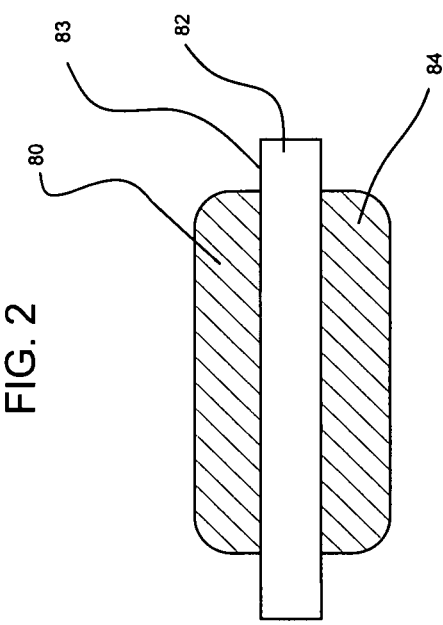
FIG. 2 is a partial longitudinal cross-sectional view taken along the line 2-2 of FIG. 1.
Figure 3:
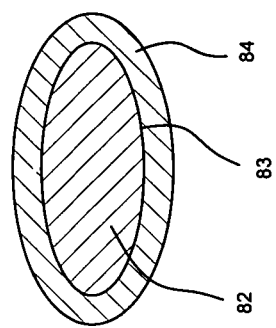
FIG. 3 is a partial transverse cross-sectional view taken along the line 3-3 of FIG. 1.
Figure 4:
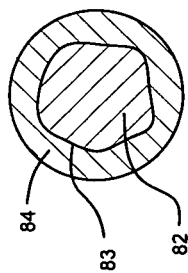
FIG. 4 is a transverse cross-sectional view of a food product having a generally elliptical or generally oval configuration.
Figure 5:
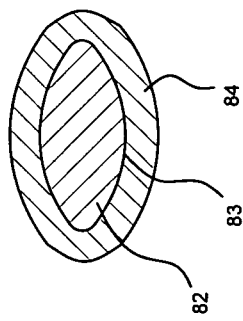
FIG. 5 is a transverse cross-sectional view of a food product having a generally round or generally circular configuration.

Nevertheless, pet treats for dogs that resemble bones are well-received not only by pet owners but also by their pet dogs. To that end, a pet treat according to the present invention may be shaped similarly to a beef rib with meat still attached, see FIG. 1. For example, the treat may include an inner component 82 shaped like a bone (see FIGS. 1 and 2). In transverse cross section, the inner component 82 may be generally oval or generally double-convex (see FIG. 3), generally elliptical or generally oval (see FIG. 4), generally circular or generally round (see FIG. 5), generally polyhedral (see FIGS. 6 and 7), or any other desired shape or configuration. The outer component 84 may surround or encase a lateral surface 83 of the product, or may substantially surround or encase the lateral surface 83 (see FIG. 8).

As may be desired, the inner bone-like component may include ingredients to provide a color resembling natural bones. Preferably, the bone-like inner component has a moist, chewy texture that is flexible and compressible. To provide an interesting taste for the dog, the inner component may include meat products, sweeteners, and flavorants.

The lateral surface 83 of the inner component 82 is preferably surrounded by an outer meaty component 84, as noted. In a preferred embodiment, the meaty component 84 has a length less than the length of the bone-like portion 82 so that the ends of the bone-like portion 82 protrude beyond the meaty component 84. Typically, the length of the treat 80 is lies in the range of about 2 to about 4 times the maximum transverse dimension of the preferred embodiment of the treat 80 giving the treat an elongated appearance. In an even more preferred embodiment, the maximum transverse dimension is about 2.5 times the maximum transverse dimension. The taste and texture of the outer meaty component 84 are different from the taste and texture of the inner bone-like component 82. More particularly, the outer meaty component 84 may be moist and compressible. To provide an interesting taste for the dog, the outer meaty portion 84 preferably comprises meat products, sweeteners, and flavorants as much as 85 wt %.

To balance tastes and textures of the inner and outer components, the inner component 82 preferably comprises about 40 to about 80 wt % of the treat, while the outer component 84 comprises about 60 to about 20 wt % of the treat. More preferably, the inner component 82 and the outer component 84 are substantially balance with each being about 50 wt % of the treat.

Figure 9:
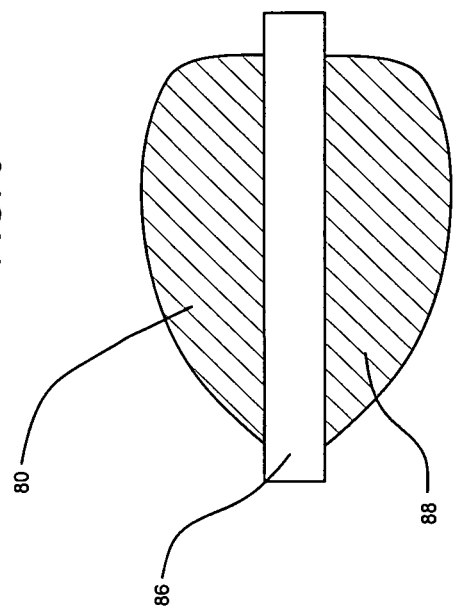
FIG. 9 is a partial cross-sectional view of a second embodiment of a pet treat made by the process of this invention.

While the foregoing describes a preferred embodiment of the food item such as a pet treat, other configurations are within the spirit and scope of the invention. For example, see FIG. 9, an inner bone-like component 86 may be substantially surrounded by a bulbously shaped outer meaty portion 88. Again, the ends of the inner portion 86 preferably protrude longitudinally from the outer meaty portion 88. Nevertheless, it is within the contemplation of this invention that one end of the inner bone-like portion 86 is covered by the outer meaty portion so that the treat resembles a ham bone with ham thereon.

If desired, the outer meaty portion could be arranged so that is contains a plurality of bone-like inner components, so that the pet treat resembles a rack of ribs with meat connecting the ribs (i.e., the inner bone-like portions). Such a configuration provides the pet owner the flexibility to offer the pet multiple portions of the pet treat. Alternatively, the number of "ribs" may be used a mechanism to adjust the portions of the treat for dogs according to their different size and/or weight.

The inner bone-like component 82 may be fashioned from a mixture of ingredients. Preferably, the recipe for the inner component includes ingredients in the ranges set forth in the following table.

| Inner Component Ingredients, wt % | | |
|---|---|---|
| | Min. | Max. |
| Water | 0% | 24% |
| Meats | 0% | 30% |
| Soy | 0% | 17% |
| Sweetener | 0% | 24% |
| Gelatin | 0% | 10% |
| Wheat Gluten | 0% | 7% |
| Preservatives | 0% | 4% |
| Starch | 0% | 4% |
| Flavorants | 1% | 18% |
| Acidulent | 0% | 2% |
| Salt | 1% | 6% |
| Colorants | 0% | 1% |
| Grain | 0% | 69% |
| Fiber | 0% | 7% |
| Humectant | 0% | 10% |
| Fat or Oil | 0% | 5% |
| Enzyme | 0% | 1% |

Similarly, the meaty outer component 84 may also be fashioned from a mixture of ingredients. Preferably, the recipe for the outer component includes ingredients in the ranges set forth in the following table.

| Outer Component Ingredients, wt % | | |
|---|---|---|
| | Min. | Max. |
| Meats | 0% | 68% |
| Soy | 0% | 20% |
| Sweetener | 0% | 18% |
| Flavorants | 1% | 6% |
| Preservatives | 0% | 2% |
| Salt | 1% | 5% |
| Colorants | 0% | 1% |
| Grain | 0% | 34% |
| Water | 0% | 12% |
| Humectant | 0% | 5% |
| Wheat Gluten | 0% | 5% |
| Starch | 0% | 4% |
| Fiber | 0% | 4% |
| Acidulent | 0% | 1% |

Suitable materials for the "meats" used in the recipes include meat and meat by-products including, but not limited to, mechanically deboned beef, boneless beef, beef lungs, beef liver, beef fat trim pork, pork lungs, pork liver, venison, lamb; poultry and poultry by-products including, but not limited to, chicken, turkey; fish and fish by-products including, but not limited to, tuna, salmon, ocean whitefish, shellfish, and the like; as well as combinations of two or more thereof. The soy ingredient may include soybean meal, soybean flour, soy grits, soy protein concentrate, and the like, as well as combinations of two or more thereof. Suitable sweeteners include fine sugar, corn syrup, maltodextrin, or the like as well as combinations of two or more thereof. Suitable preservatives used in the recipes include potassium sorbate, sodium nitrite, mixed tocopherols, BHA, and the like, as well as combinations of two or more thereof. Suitable starch for the recipes includes corn starch, food starch, and the like, as well as combinations of two or more thereof. Useful flavorants for the recipes include natural and/or artificial smoke flavor, cheese powder, dry cheddar cheese, onion extract, onion salt, garlic powder, animal digest, blood plasma, food flavors, and the like, as well as combinations of two or more thereof. Suitable acidulents include phosphoric acid, citric acid, and the like, as well as combinations of two or more thereof. For purposes of the recipes, salt may include sodium chloride, calcium sulfate dehydrate, salt flour, bone phosphate, and the like, as well as combinations of two or more thereof. Suitable colorants for the recipes include FD&C Red #40, caramel color, titanium dioxide, other FD&C colors, and the like, as well as combinations of two or more thereof. Suitable grains for the recipes include wheat, wheat flour, ground rice, wheat middlings, and the like, as well as combinations of two or more thereof. To provide fiber, cellulose fiber, or the like may be used. Suitable humectants for the product include propylene glycol, glycerin, and the like, as well as combinations of two or more thereof. Liquipanol T may function as an enzyme in the recipes.

Typically, the moisture in both the inner and outer parts lies in the range of 7 to 35%, and the water activity at equilibrium is below about 0.76. For purposes of this invention, water activity may be measured by Rotronic equipment having an overall accuracy of ±0.01 R.H.

A preferred example of the composition for the inner part of the pet treat includes the following ingredients: water at about 23.6 wt %; beef at about 21 wt %; soy at about 17 wt %; sweetener at about 11 wt %; gelatin at about 9 wt %; wheat gluten at about 7 wt %; preservatives at about 0.4 wt %; propylene glycol at about 3 wt %; starch at about 4 wt %; flavorants at about 1.3 wt %; an acidulent at about 1.3 wt %; and colorants at about 0.2 wt %.

A preferred example of the composition for the outer meaty part of the pet treat includes the following ingredients: beef products at about 64 wt %; soy at about 19 wt %; sweetener at about 1.7 wt %; flavors at about 1.6 wt %; preservatives at about 1.5 wt %; and colorants at about 0.3 wt %.

The pet treat of this invention preferably has a meaty outside portion and exhibits a smoke flavor having desirable palatability for dogs. More particularly, the outer portion can have a meat content approaching 68 wt %. In addition, the pet treat has an inner bone-like portion also having a meaty palatability and a gel matrix structure accomplished by a combination of gelatin, maltodextrin, starch and wheat gluten.

The process of this invention can be used to manufacture edible food products for consumption by humans, animals, or pets. The particular food product may be fashioned using recipes specific to the ultimate consumer, and may have flavors tailored to the ultimate consumer. Where the ultimate consumer is human, the production facility may need license and/or approval from the USDA.

Figure 10:
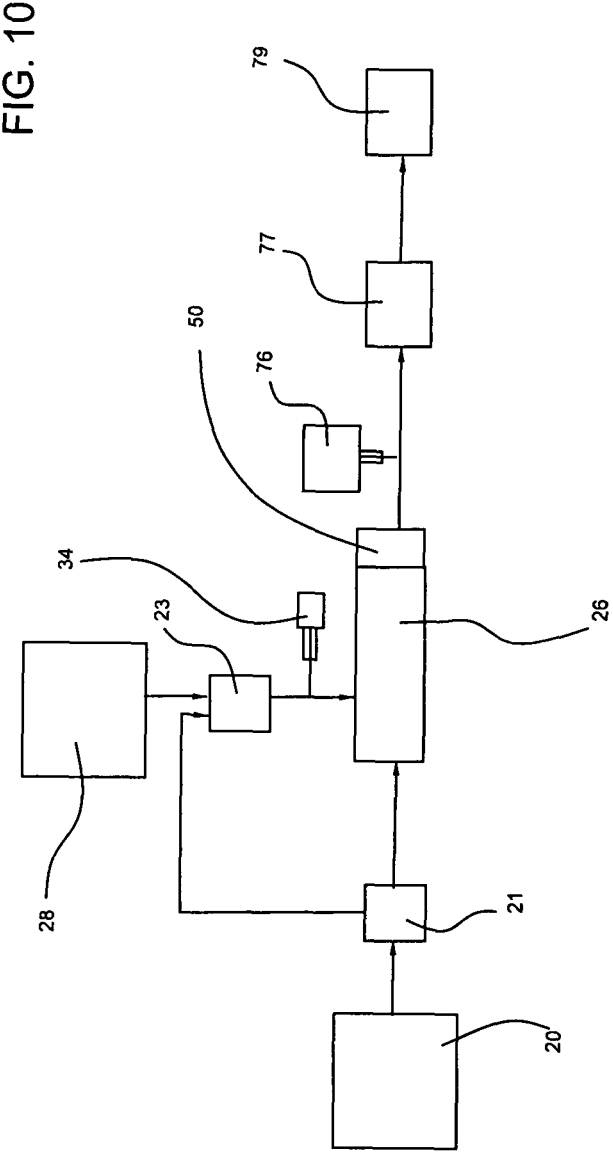
FIG. 10 is a schematic diagram of the intermittent flow process for making a food product.

By way of example, the process will be described in connection with manufacture of the unique pet treats described above by a substantially continuous process. As the components of the food product are shaped by a forming manifold 26 (see FIG. 10), the composition for a first or inner component of the product is supplied to the forming manifold 26 by a suitable device 20. Ingredients for the bone-like inner component of the pet treat described above are mixed together to thoroughly blend them and form a highly viscous first composition. At substantially the same time, the composition of a second or outer component of the product is prepared and supplied to the forming manifold 26 by a second suitable device 28. The ingredients for the outer component, which may be meaty, are also mixed together to thoroughly blend them and form a highly viscous second composition. Both the first and second compositions are then delivered or supplied under pressure to a forming manifold. If desired, the first device 20 for mixing and delivery of the first composition can be accomplished through use of a pump, an extruder, a cooking extruder, a twin-auger feeder, or similar device. Likewise, the second device 28 for mixing and delivery of the second composition can be accomplished through use of a pump, an extruder, a cooking extruder, a twin-auger feeder, or similar device. A suitable pump may, for example, comprise a rotary positive-displacement pump, such as the Waukesha Cherry-Burrell Universal I Series pump, for either or both devices 20, 28.

In some instances, it may be desirable to include a portion of the first composition in the second composition. To that end, the discharge of the first device 20 may enter an optional conventional splitting device 21 to divert a portion of the first composition to a mixer 23 positioned between the discharge of the second device 28 and the forming manifold 26. The mixer 23 may be a static mixer to intermix the diverted portion of the first composition with the second composition. Such an arrangement may be useful to, for example, to provide a marbled appearance for the outer component.

At the forming manifold 26, the first composition is divided or split into a plurality of core streams. Each core stream of the first composition is delivered to a corresponding forming die. The forming manifold also divides or splits the second composition into a corresponding plurality of secondary streams. Each secondary stream of the second composition is formed within the manifold into an annular tubular flow which surrounds a corresponding one of the core streams. The manifold includes a forming die for each tubular flow so that the second composition moves into lateral contact with the corresponding core stream as the tubular flow and the core stream discharge from, or extrude from, the die and the forming manifold.

At this point in the process, the secondary composition of the tubular flow substantially encases the primary composition of the core flow. To obtain the desired "rib" shape for the pet treat of this invention, the tubular flow of the secondary composition is periodically interrupted. To accomplish that interruption, a gate valve assembly 50 is preferably provided downstream of the forming manifold to intermittently control the flow of the second composition from the forming manifold 26 to obtain the uniquely configured products described above. The gate valve assembly may include a pair of reciprocal knife plates located at the discharge orifice of the forming manifold. The knife plates are constructed and arranged such that in one position they simultaneously cover the discharge orifices for the secondary tubular flows while not affecting the discharge orifices for the core streams. In a second position, the knife plates are arranged such that they do not affect the discharge of either the tubular flows or of the core streams. By advancing the knives to the first position for a first time interval, and moving the knives to the second position for a second time interval, a continuous stream of the first composition is periodically surrounded by a sheath of the second composition. The cross-sectional shape of the continuous stream and the sheath are defined by the shape of the corresponding die orifices of the forming manifold.

From the gate valve assembly 50, the product is delivered to a cutting assembly 76 where individual products are separated from a continuous product. Thereafter, the individual products move to a drying operation 77, and then to a packaging operation 79.

The continuous stream of the first composition may be severed at locations preferably between the sheaths of the second composition to divide the continuous product flow into individual pieces. The individual pieces are then allowed to dry for a predetermined period of time.

In some packaging applications 79, the individual pieces may be individually packaged. In other applications, multiple individual pieces may be packaged in hermetically sealed containers or pouches. Preferably, the containers or pouches are re-sealable so as to preserve freshness and consistency in the pet treats during use.

Use of a conventional cooking extruder for pressurization and delivery of the second composition has been found to shorten the drying time for the resulting pet treat. In fact, the drying time for the pet treat fabricated using a cooking extruder for the second composition has been observed to be approximately 50% of the drying time for the pet treat fabricated using a positive displacement pump. Nevertheless, use of a positive displacement pump is presently preferred because the resulting product exhibits flavor associated with slow cooking and because the resulting product has a consistent texture substantially free of a hard outer surface.

Figure 11:
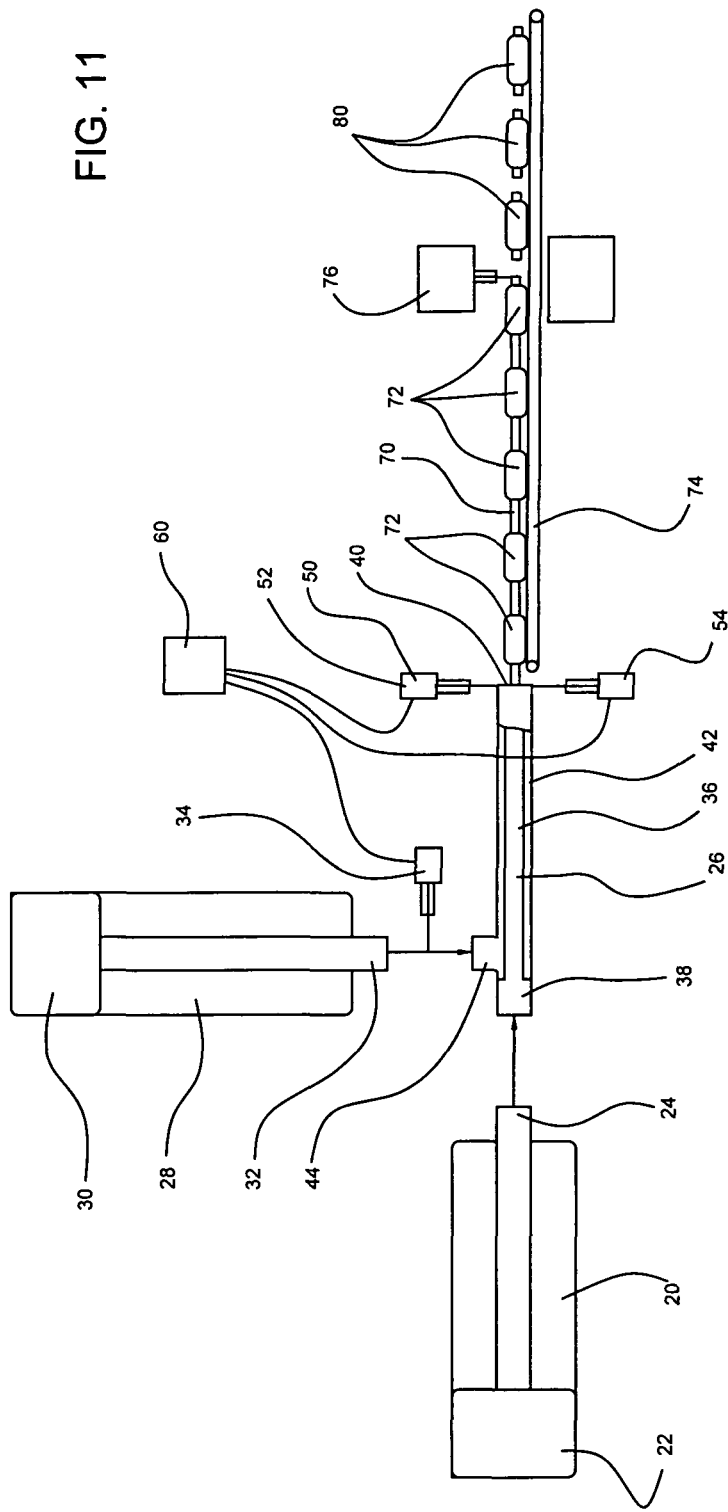
FIG. 11 is a schematic diagram of the intermittent flow extrusion process for making a pet treat.

Turning to FIG. 11, an embodiment of the process for making pet treats according to the present invention with extruders is schematically depicted. The first extruder device 20 may be used to process the inner part or component of the resultant product. A suitable conventional Bonnot extruder may, for example, be used. However, other types of single screw and twin screw extruders from Wenger, Clextral, Werner-Pfleiderer, etc. can be used. Alternatively, devices other than an extruder can be used. For example, a pump such as a Waukesha, Doring, or Moyno pump is suitable. Likewise, a device such as a Vemag twin auger stuffer can be used where the ingredients are to be cooked later.

Ingredients for the inner bone-like component are supplied to an inlet end 22 of the first extruder device 20. Within the first extruder device 20, those ingredients are blended, plasticized, and delivered to a discharge end 24. From the discharge end 24, the plasticized first component advances directly to a product-forming manifold 26.

A second extruder device 28 processes ingredients for an outer meaty part or component of the resultant product. Here again, a suitable conventional Bonnot extruder or other pump, or auger stuffer, or extruder may be used. Outer component ingredients may be supplied to the inlet end 30 of the second extruder 28. Within the second extruder device 28, those ingredients of the outer component may be blended, cooked or plasticized, and delivered to its discharge end 32. From the discharge end 32 of the second extruder device 28, the plasticized second component advances to the forming manifold 26; however, flow of the second component from the second extruder device 28 to the forming manifold 26 is subject to control by a gate valve 34.

One embodiment of the forming manifold 26, shown in partial cross section in FIG. 11, is preferably constructed and arranged so that the second component surrounds first component. This embodiment is constructed and arranged to make individual products from a single shaping orifice. To that end, the forming manifold 26 includes a central channel 36 extending from an inlet chamber 38 to a discharge end 40. At the discharge end 40, the manifold may include a die orifice to shape the cross section of the resulting extrudate. That orifice may have a generally round shape, a generally oval shape, a generally elliptical shape, a generally convex shape, a generally polyhedral shape, or any desired configuration; however, an oval or generally elliptical shape is preferred. A second channel 42 directs flow of extrudate from the second extruder device 28 to the discharge end 40 of the forming manifold 26. The second channel 42 extends from a lateral inlet chamber 44 to the discharge end 40 of the forming manifold 26. Preferably, the second channel 42 surrounds the central channel 36 thereby contributing to reduced heat loss from the central channel 36. The discharge end 40 of the forming manifold 26 may also include a shaping orifice for the outer component.

A double gate valve 50, located at the discharge end 40 of the forming manifold 26, may include an upper actuator unit 52 and a lower actuator unit 54. The double gate valve 50 is operable to interrupt or stop flow of extrudate from the second channel 42 while allowing uninterrupted flow of extrudate from the central channel 36. Instead of a double gate valve, a ball valve, plug valve, or other suitable valve can be used.

Operation and sequencing of the gate valve 34 and the double gate valve 50 are controlled by a programmable logic controller and/or cycle timer 60. With that control circuitry, the inner component is discharged from the manifold 26 as a substantially continuous member 70. Moreover, with that control circuitry, the outer component is discharged from the manifold 26 intermittently so that bulbous deposits 72 are made around the rope-like continuous member 70 at uniformly spaced locations. The bulbous deposits completely surround the rope-like continuous member and require no additional forming after discharge from the die. The composite product, comprising the substantially continuous member 70 and the bulbous deposits 72, is supported and advanced by a suitable conventional conveyor 74 to a suitable conventional cutting station 76. The cutting station 76 may, for example, include a guillotine cutter, a rotary cutter, or an ultrasonic cutter. At the cutting station 76, the substantially continuous member 70 is severed between adjacent bulbous deposits 72, thereby making individual treats 80. Depending upon the desired product, the cut can be made to produce equal length projections from the adjacent pieces, or unequal length projections. Those individual treats 80 then move to further processing, packaging, and distribution stations.

The control circuitry 60 operates the first valve 34 to stop flow from the second extruder 28 and relieve pressure in the extrudate that is delivered to the manifold 26 and which ultimately forms the outer component. The control circuitry 60 also operates the double gate valve 50 to prevent dribbling of the outer component extrudate onto the extrudate from the central channel 36 of the manifold 26. Thus, by controlling the length of time that both the gate valve 34 and the double gate valve 50 are closed, the control circuitry 60 also determines the length of the inner extrudate, which is exposed between the bulbous deposits 72.

If desired, the first gate valve 34 may include a modulating function. Alternatively, a separate modulating valve may be interposed between the second extruder 28 and the manifold 26. By means of such a modulating function, or modulating valve, flow of the outer component can be controlled by the control circuitry 80 to vary the cross-sectional thickness of the bulbous deposits 72.

As a result, the individual treats 80 may be designed to have a variety of unique and novel configurations. For example, the individual treats 80 may be shaped like small hams, small roasts, small legs of lamb, and other configurations where a bone protrudes from one or both ends. An individual treat 80 (see FIG. 2) shaped like a rib may include an inner part 82 having an oval cross section and projecting at both ends from the bulbous deposit shaped like a substantially constant thickness piece of meat 84. If desired, the inner part may be colored to resemble a bone while the outer part includes coloration to resemble meat.

After the product has been formed, it is dried before packaging. Presently, the drying is effected over about 8 to about 9 hours at a temperature ranging from about 140° to about 180° F. Temperatures exceeding that range may shorten the drying time but have been observed to cause cook-out of ingredients such as fats and produce a resulting deleterious affect on appearance. The preferred drying conditions provide slow cooking for the meat in the product while substantially avoiding case hardening of the product components.

One of the many advantages of the process of this invention concerns the substantial elimination of any post-extrusion forming steps to shape, mold, or otherwise configure the resulting product. Avoiding such post-extrusion forming steps reduces the capital requirements for processing equipment and also reduces the need for personnel to monitor and operate such post-extrusion forming equipment. Accordingly, the food products of the present invention may be prepared economically.

Figure 12:
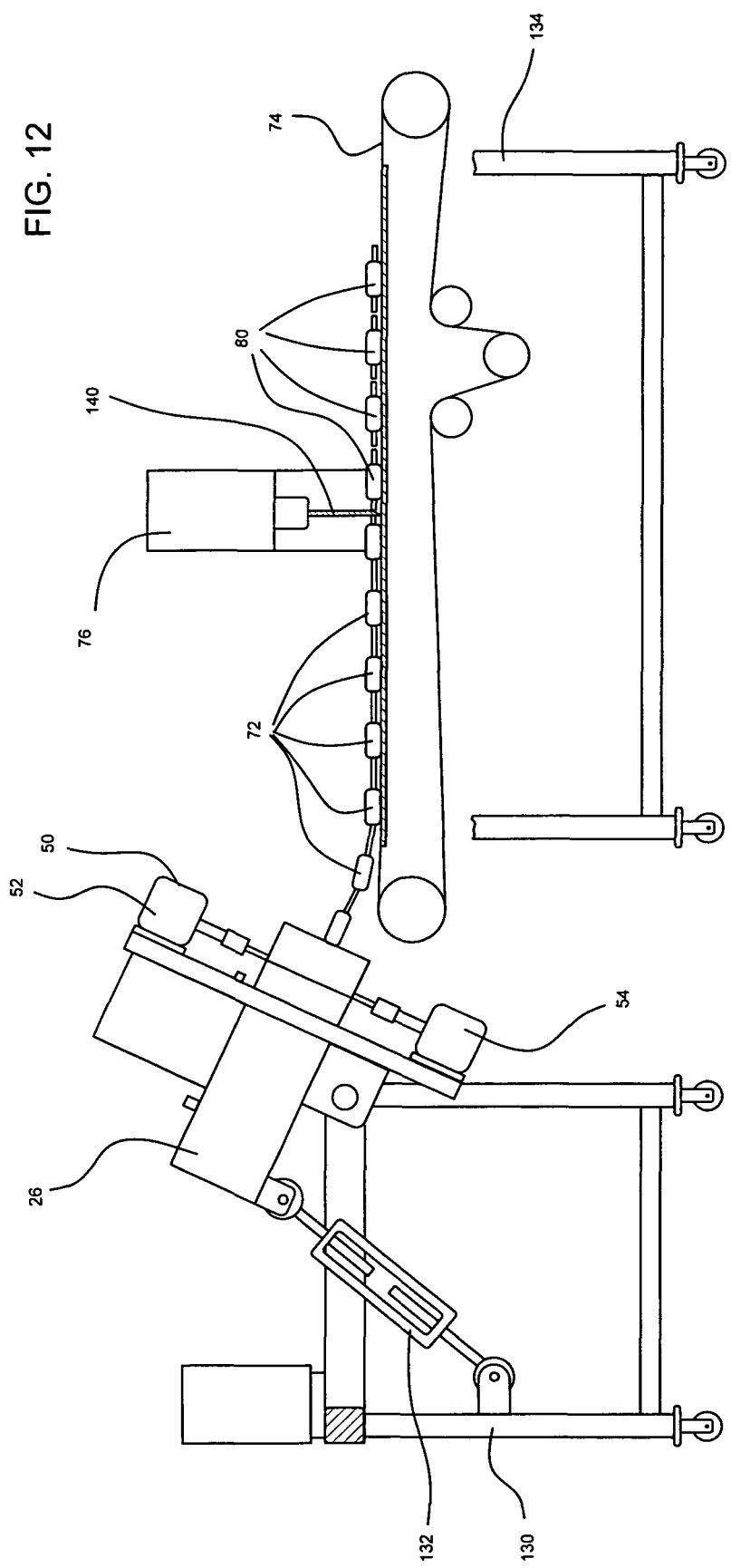
FIG. 12 is a partial side elevation view of a process for making a pet treat according to the process of this invention.

More details of the process are shown in FIG. 12. As shown, the gate valve assembly 50 may be attached directly to the discharge face, or plane, of the forming manifold. Moreover, the forming manifold 26 may be mounted to a movable carriage 130. The forming manifold 26 may be pivotally connected to the movable carriage 130 so that the elevation and position of the manifold discharge can be moved vertically and/or horizontally relative to the receiving conveyor 74. In this way, the product leaving the forming manifold 26 can be delivered to the conveyor 74 with little or no stress or strain being imposed on the as yet undried product. To securely hold the forming manifold 26 in a desired position relative to the carriage 130, a conventional turnbuckle 132 may be attached between the carriage 130 and an end of the forming manifold 26.

The conveyor 74 which receives undried product from the forming manifold may be carried on a post-forming carriage 134 that may be movable to facilitate positioning of the conveyor in close juxtaposition to the discharge from the forming manifold 26. The cutting mechanism may also be mounted on the post-forming carriage 134. While a variety of cutting mechanisms are suitable for use in the process, an advantageous device is an ultrasonic knife 140. Ultrasonic vibrations of the knife 140 discourage the composition of the inner component from sticking to, or otherwise becoming attached to, the knife 140 itself. To provide higher production speeds, the knife 140 may be mounted in the assembly 76 so as to synchronously move in the direction of travel of the conveyor 74. More particularly, the assembly 76 preferably operates such that the knife 140 moves in substantially the same direction and at substantially the same speed as the conveyor 74 and the knife 140 moves downwardly during a cutting stroke to cut or sever individual pieces from the continuous product issuing from the forming manifold 26. Further, the assembly 76 moves the knife 140 back toward the forming manifold 26 between cutting strokes.

Figure 13:
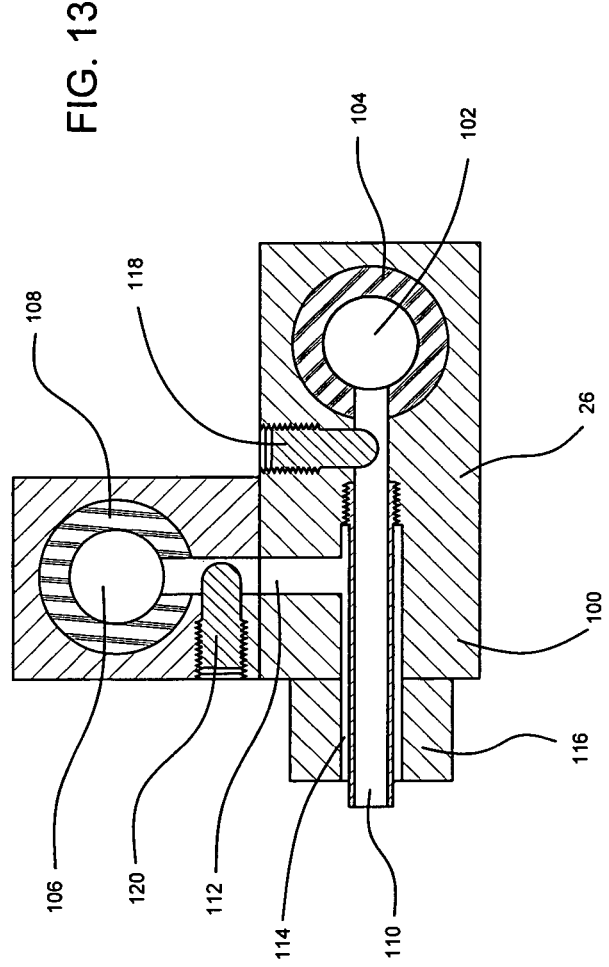
FIG. 13 is a cross-sectional view of one embodiment of a manifold for forming a product.

One embodiment for the forming manifold 26 is shown in FIG. 13. This embodiment includes a channel 102 in fluid communication with the first delivery device 20 and is operable to receive the first composition under pressure. The channel 102 may include an insert 104, fabricated from acetal resin (e.g., "Delrin") and/or tetrafluroethylene (e.g., "Teflon"). The embodiment also includes a second channel 106 in fluid communication with the second delivery device 28 and is operable to receive the second composition under pressure. The second channel 106 may also include an insert 108 fashioned from acetal resin and/or tetrafluroethylene. A die tube 110 may be threadably attached to the manifold 26 in longitudinal alignment and in fluid communication with the first channel 102. The die tube 110 has a cross-sectional configuration selected to define the shape of the inner part of the product. The second channel 106 communicates with a substantially annular channel 114 surrounding the die tube 110 and extending through a die block 116. The die block 116 shapes the outer part of the product.

A first control pin 118 is positioned so as to be able to control flow from the first channel 102 through the die tube 110. A second control pin 120 is positioned so as to be able to control flow from the second channel 106 to the annular channel 114. The control pins 118, 120 can be operated manually to adjust the extrudate flow through the die tube 110 and the annular channel 114, respectively. Moreover, the control pins 118, 120 can be provided with corresponding controllable actuators (not shown) which are operable to move the control pins between fully open positions and fully closed positions to open or close flow to the associated die tube 110 and die channel 114. Further, actuators for the control pins 118, 120 may also be modulated so as to adjust the flow in the associated die tube 110 and annular channel 114 to controllable values between fully closed and fully open. In this manner the cross-sectional shape of both the inner and outer part can be regulated and/or varied.

Figure 14:
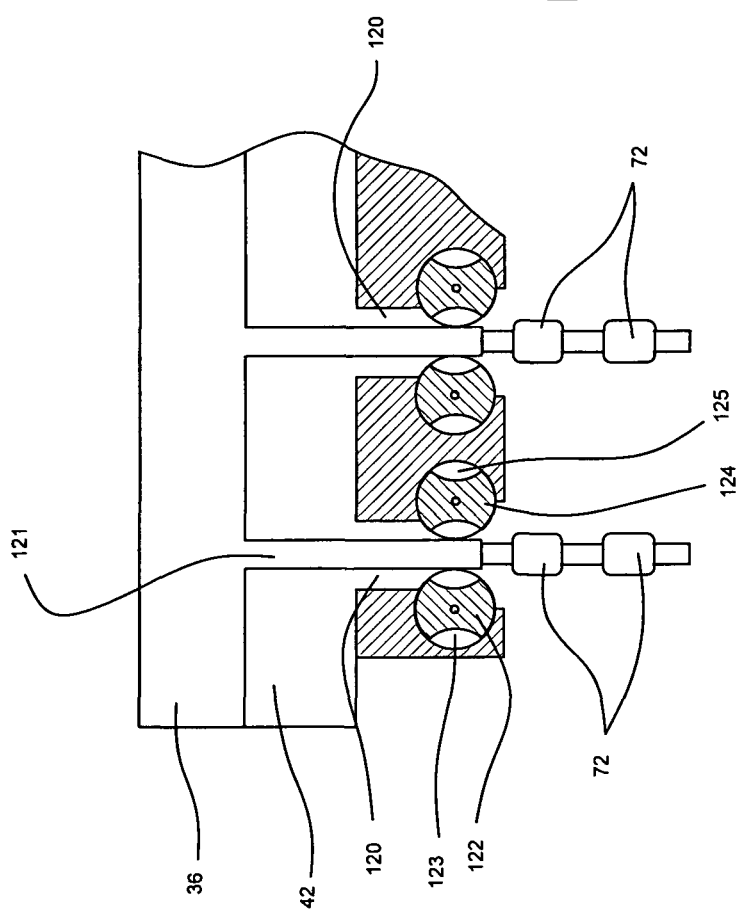
FIG. 14 is a partial cross-sectional view of a second embodiment of a manifold for forming a product.

In commercial operations, it may be desired to provide multiple product production orifice assemblies for the forming manifold 26, see for example FIG. 14. The multiple product streams can be operated alternately so as to reduce and possibly eliminate pressure surges in the manifold due to interruption of extrudate flow for the outer part. More particularly, if the extrudate passes through four orifices and, when that flow is interrupted switches to four additional orifices of the same shape and size, then the flow continues virtually unabated and pressure surges back through the system are virtually eliminated.

In addition to the double gate valve discussed above, extrudate flow for the outer part can be controlled in other ways. For example (see FIG. 14), a discharge channel 120 for the second extrudate surrounds a discharge tube 121 communicating with the central channel 36. To control extrudate flow through the discharge channel 120, a pair of counter-rotating cams 122, 124 is provided. Each cam 122, 124 includes one or more pockets 123, 125, respectively. The counter-rotation of the cams 122, 124 may be controlled so that the pockets 123, 125 move symmetrically into and out of mutually opposed positions relative to the discharge tube 121. When the pockets 123, 125 are rotated to a position 90° from the position shown in FIG. 14, the cams 122, 124 interrupt flow through the channel 120. Thus, the co-extrusion process generates the bulbous deposits 72 of the outer part on the substantially continuous inner part.

Figure 15:
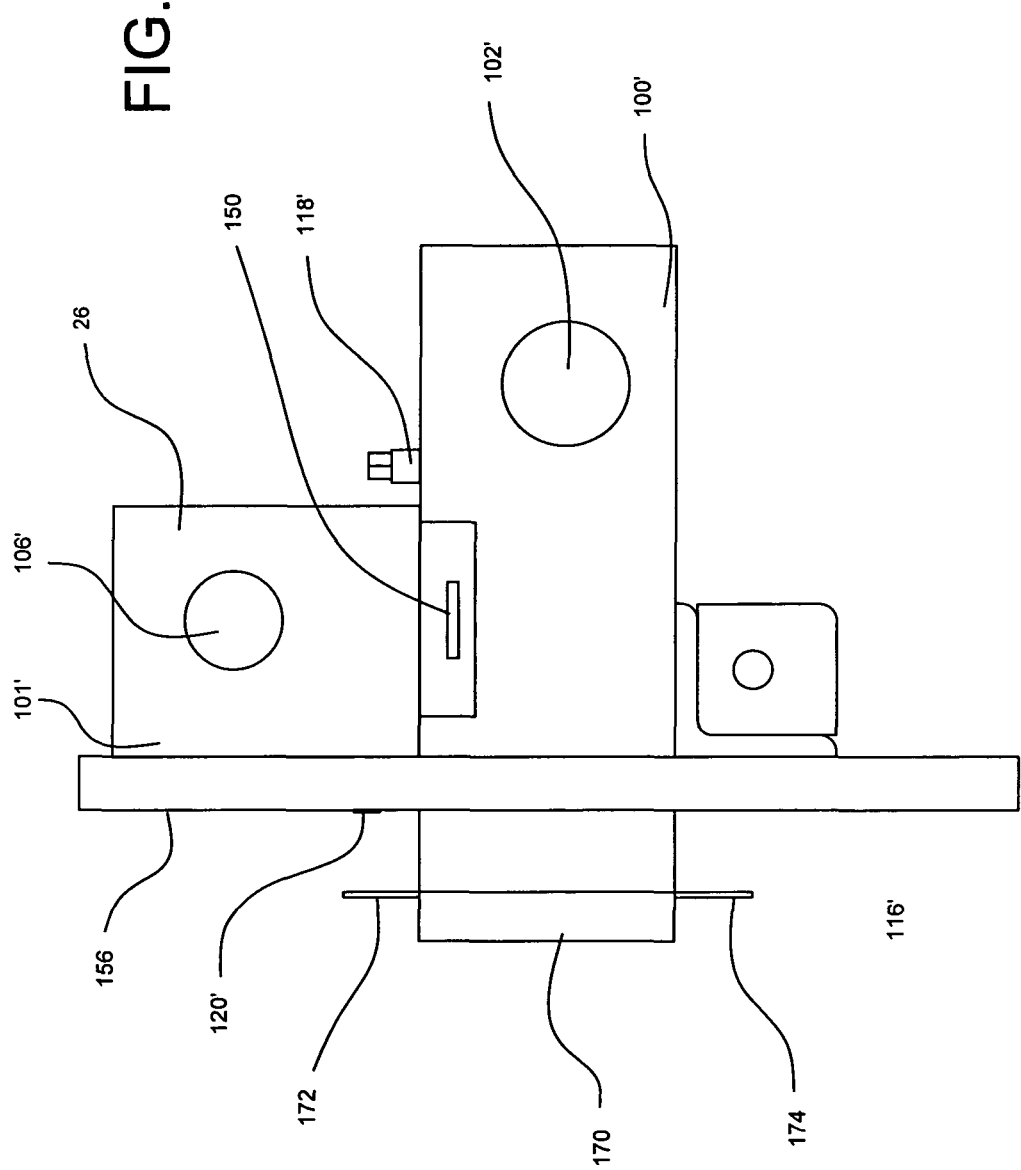
FIG. 15 is side view of the manifold used in the process of FIG. 12.

A side view of a forming manifold 26 suitable form simultaneously producing a plurality of food products according to the invention is shown in FIG. 15. The forming manifold 26 includes body elements 100', 101' that are secured together in conventional fluid tight manner. Together, the body elements 100', 101' form the manifold body. The manifold body has a first channel 102' for receiving the first composition under pressure, and a second channel 106' for receiving the second composition under pressure. Both channels 102', 104' may extend from side to side of the manifold body. One end of each channel 102', 104' is closed by a conventional plug or cap (not shown) so that the manifold body directs the flow and distribution of the composition to the discharge face or plane 156.

Figure 16:
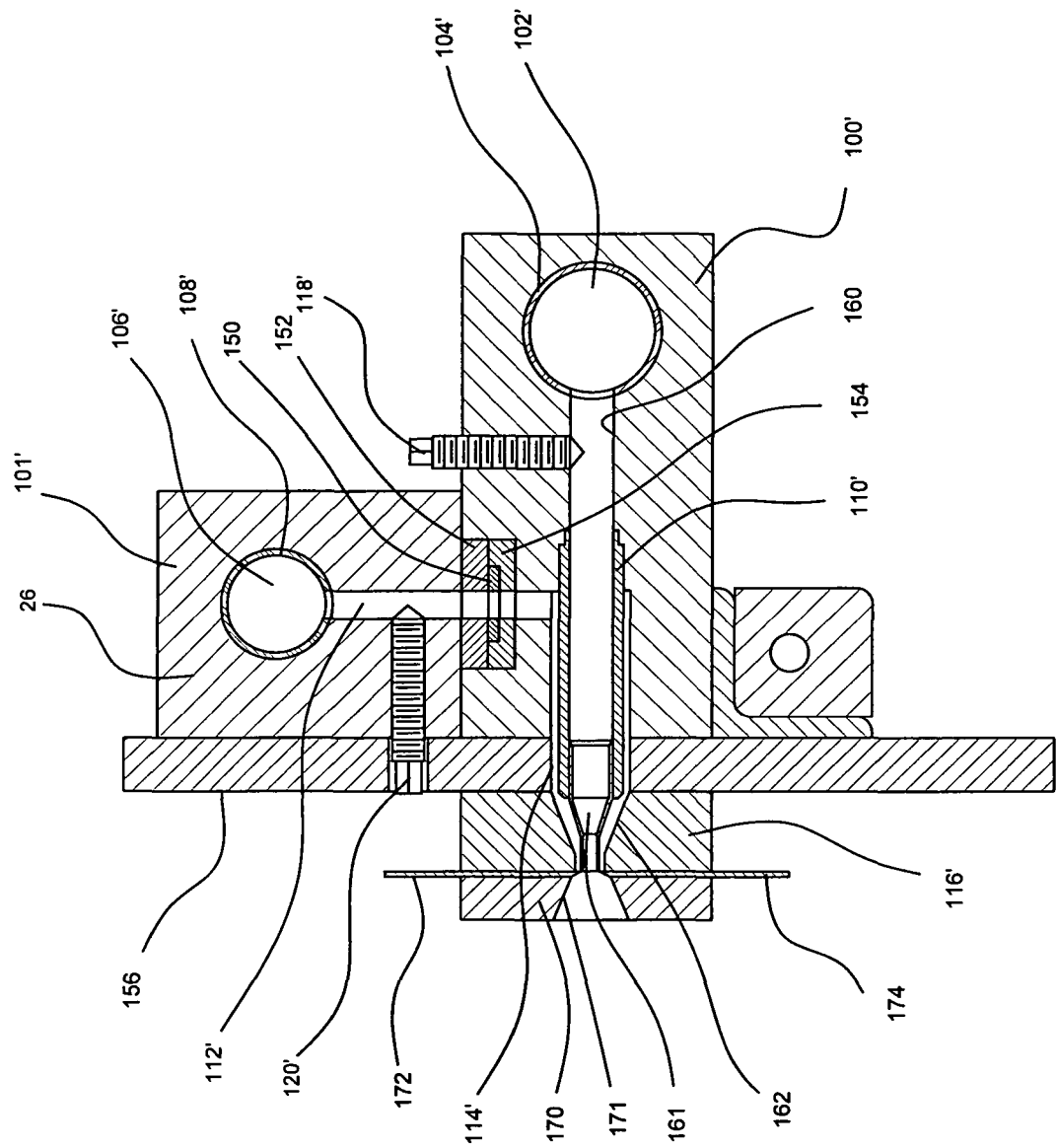
FIG. 16 is a cross-sectional view taken along the line 16-16 of FIG. 17.

The manifold body may be provided with an internal slide valve assembly including a slide valve plate 150 that is accessible from the side of the manifold body so that it can be operated reciprocably. The slide valve assembly also includes pair of guide strips 152, 154 (see FIG. 16) which may be mounted in a groove of the body element 100' and which may be held in place by the two body elements 100', 101'. The guide strips 152, 154 may be fabricated from acetal resin and/or tetrafluroethylene, as desired. The slide valve plate 150 has a plurality of orifices which are alignable with the channels 112' and which conform to the cross-section of those channels. Accordingly, in one position where the orifices of the slide valve plate 150 align with the channels 112' fluid can move through the channels. However, in a second position where the orifices of the slide valve plate 150 are not aligned with the channels 112', fluid communication through those channels is interrupted. In short, the slide valve plate 150 is operable to permit, not permit, and/or regulate flow through the channels 112'.

The first channel 102' may have an acetal resin or tetrafluroethylene liner 104', and communicates with one end of a branch channel 160 that extends beyond the discharge face 156 of the forming manifold 26. At least part of the branch channel 160 is formed by a die tube 110', An annular channel 114' is provided within the manifold body around the die tube 110' and the branch channel 160. The annular channel 114' extends to the discharge face of the forming manifold 26.

The second channel 106' may have also include an acetal resin or tetrafluroethylene liner 108'. In addition, the second channel 106' communications with a passage 112' which, in turn, communicates through the slide valve assembly 150 with the annular channel 114'.

A control pin 118' connects with the branch channel 160 and may be operable to control and/or modulate flow through the branch channel 160. Similarly, a control pin 120' connects with the passage 112' and may be operable to control and/or modulate flow through the passage 112'.

The downstream end of the die tube 110' may be provided with an orifice tube 161 that includes an exit orifice shaped as may be desired to define the cross sectional configuration of the inner component. A die block 116' is attached to the discharge face 156 of the manifold body and includes an internal convergent surface 162 which cooperates with the orifice tube 161 and the die tube 110' to define an internal convergent passage that communicates at one end with the annular channel 114' and, at the other end, surrounds the orifice of the orifice tube 161.

Attached to the die block 116' is a valve assembly which includes a body plate 170 have an opening sufficiently wide and high that product extruded from the annular channel 114' and the branch channel 160 pass through the body plate 170 unobstructed. The valve assembly also includes a pair of reciproable, opposed valve plates 172, 174. These valve plates 172, 174 are movable between the closed position (shown in FIG. 16) and a retracted position. In the closed position, the valve plates 172, 174 are operable to occlude, prevent, or modulate fluid flow through the annular channel 114' and out of the manifold body; however, even in the close position, the valve plates 172, 174 do not impede fluid flow through the branch channel 160, the die tube 110', and the orifice tube 161. The valve plates 172, 174 may be reciprocated using pneumatic cylinders, hydraulic cylinders, of a motor-driven cam mechanism, as desired.

Accordingly, when the valve plates 172, 174 are closed, fluid flow through the die orifice of the orifice tube 161 continues unabated; but, when the valve plates 172, 174 are retracted, fluid flow occurs through both the die orifice and the annular channel 114'. As a result, a substantially continuous inner component can be continuously produced with intermittent deposits of an outer component substantially encompassing a lateral surface of the inner component.

Where the forming manifold handles highly viscous products of the type contemplated by the product descriptions above, axial spacing between the end of the orifice tubes 161 and the plates 172, 174 may be important. Where that axial spacing exceeds about 0.020 inches, the plates 172, 174 often do not provide the desired intermittent flow for the outer component where that axial spacing lies between about 0.010 and about 0.020 inches, the outer component may exhibit smearing on the inner component. Where that axial spacing is less than about 0.005 inches, intermittent flow for the outer component can be reliably attained.

Figure 17:
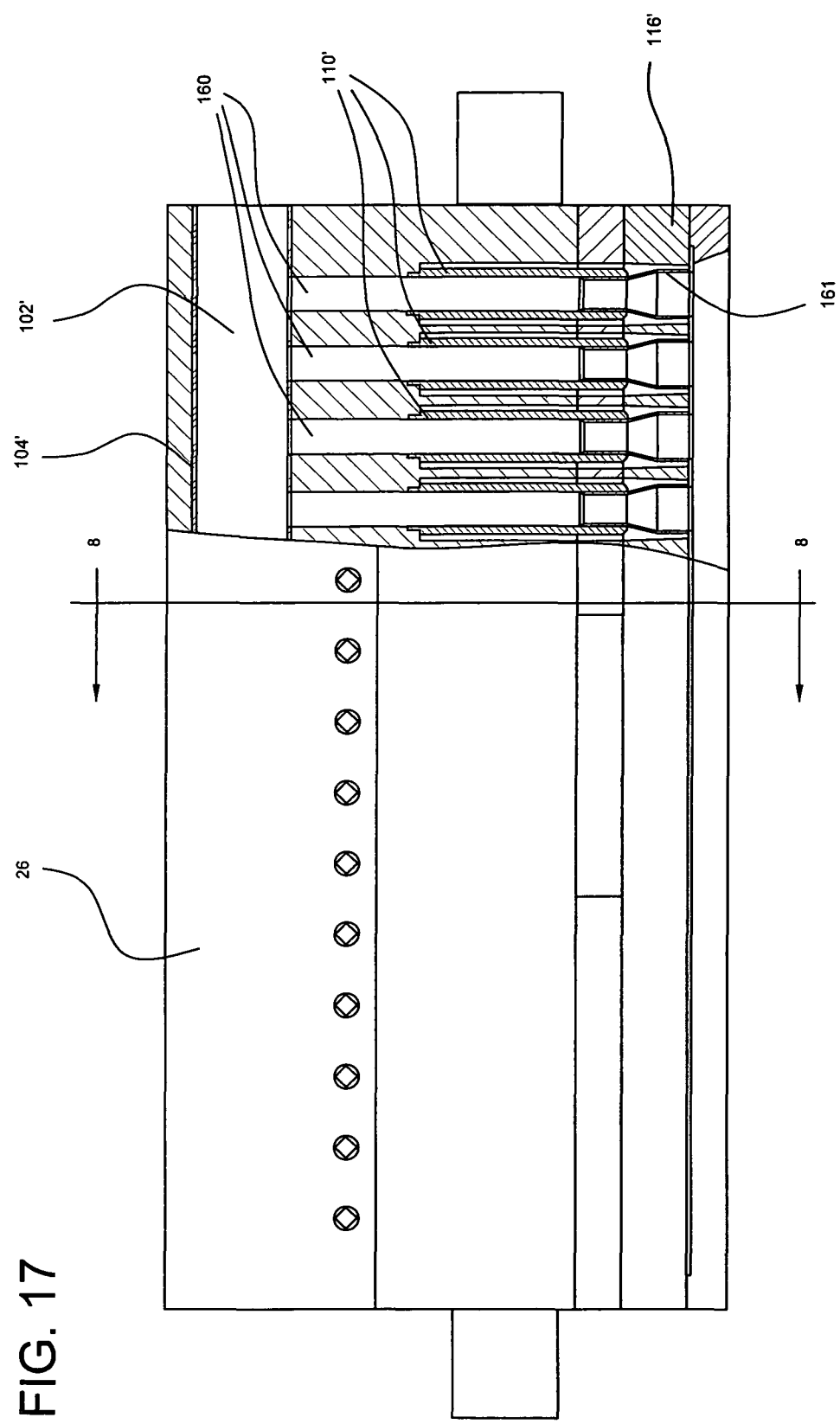
FIG. 17 is a top view of the manifold of FIG. 15 with a portion broken away to illustrate internal details.
Figure 18:
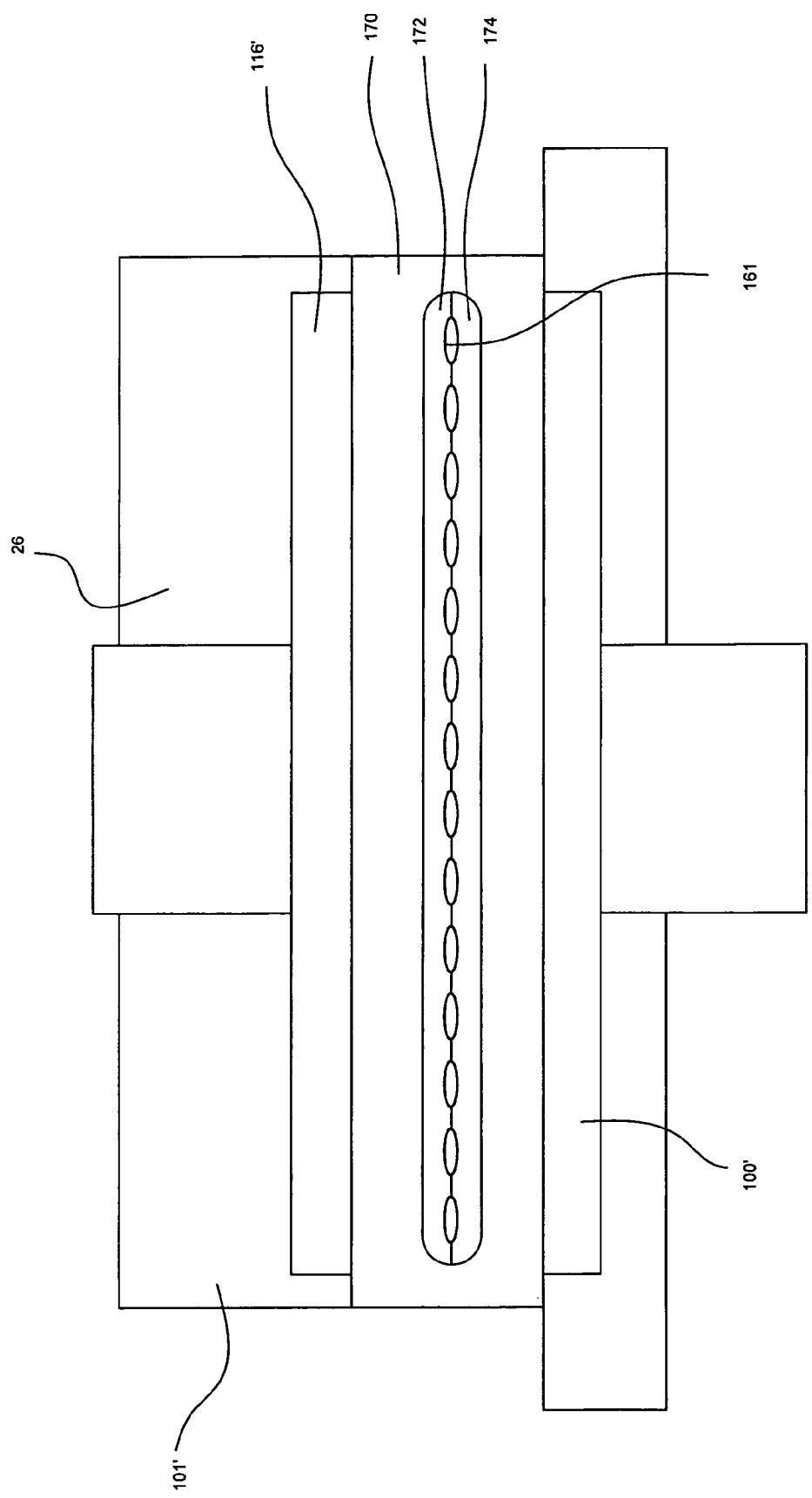
FIG. 18 is a frontal view of the manifold of FIG. 15.

Turning now to FIG. 17, it can be seen that the first channel 102' of the manifold body has fluid communication with a plurality of branch channels 160. The second channel 106' of the manifold 26 has a corresponding plurality of channels 112' (see FIG. 16). Furthermore, for each branch channel 160 (see FIG. 17), the manifold body includes the various structures and features described above. For the manifold shown, there are 14 branch channels, so 14 parallel streams of product can be produced simultaneously, as can best be seen in FIG. 18.

It will also be noted that the plates 172, 174 are constructed so that the orifice of the orifice tubes 161 are unobstructed, as described above.

From the foregoing description of the forming manifold 26, it will be seen that the first composition may be supplied under pressure from the first device 20 (see FIG. 10) to the first channel 102' (see FIG. 16) of the forming manifold 26. At essentially the same time, the second composition may be supplied under pressure from the second device 28 (see FIG. 10) to the second channel 106' (see FIG. 16) of the forming manifold 26. Within the forming manifold, the first composition is divided into a plurality of core streams, each of which passes through a corresponding branch channel 160 to be extruded from the die orifice of the corresponding orifice tube 161 attached to the manifold. The forming manifold 26 also divides the second composition into a corresponding plurality of flows, each of which passes through a corresponding channel 112', a corresponding annular channel 114', and channel 162 to substantially encase the corresponding core stream at the time they are both extruded from the forming manifold. As may best be seen in FIGS. 11-12, each core stream is substantially continuous as it leaves the manifold with a plurality of masses spaced longitudinally therealong. Thereafter, the core streams are separated to obtain individual pieces.

It will also be apparent from, for example FIG. 17, that two or more core streams of the first composition could be surrounded by a common mass of the second composition by appropriate removal of material from the die block 116' at the discharge face and between adjacent orifice tubes 161.

Various other mechanisms and techniques for interrupting flow of the extrudate for the outer part will be apparent to those skilled in the art and are intended to be within the scope of this disclosure.

Numerical values used herein are not intended to have mathematical precision. Rather, numerical values are intended to include the nominal value as well as values within a tolerance of 5% above and below the nominal value. When the word "about" is used herein with respect to a numerical value, the word "about" is intended to encompass the nominal value within typical measurement accuracy, or a tolerance of 5% above and below the nominal value, whichever is greater.

It will now be apparent that a novel extrusion process and pet treat have been described in detail. It will also be apparent to those skilled in the art that numerous modifications, variations, and equivalents exist for the various features of the novel process and pet treat, which do not materially depart from the spirit and scope of the invention. Accordingly, it is expressly intended that all such modifications, variations, and equivalents that fall within the spirit and scope of the invention, as defined by the appended claims, be within the scope of the invention as claimed.

What is claimed is:

1. A process for making a food product having an inner component and an outer component, comprising the steps of:
   supplying a first composition under pressure to a forming manifold;
   supplying a second composition under pressure to the forming manifold;
   dividing the first composition into a plurality of core streams using the forming manifold;
   dividing the second composition into a corresponding plurality of flows using the forming manifold;
   extruding the core streams through corresponding orifices of the forming manifold, each core stream having a lateral surface shaped by the corresponding orifice;
   shaping each of the plurality of flows to substantially encase the lateral surface of the core stream;
   extruding the plurality of flows through forming surfaces of the forming manifold;
   intermittently interrupting the plurality of flows while extrusion of the core streams continues so as to obtain continuous cores with a plurality of masses spaced longitudinally therealong and so as to control dribbling;
   separating the core streams between adjacent ones of the plurality of masses to obtain food products without further molding or shaping,
   wherein the step of intermittently interrupting the plurality of flows:
      stops the plurality of flows for a first time interval;
      permits the plurality of flows to discharge from the forming manifold for a second time interval; and
      sequentially repeats the stopping and permitting steps; and
   wherein the step of intermittently interrupting the plurality of flows further includes cyclically moving a pair of gates between a first position where the gates abut and occlude the plurality of flows from being discharged from the forming manifold and a second position where the gates are spaced from one another and simultaneously permit the extruding of the plurality of flows onto the plurality of core streams wherein the step of intermittently interrupting the plurality of flows further includes operating a first valve to stop flow of the second composition to the forming manifold so as to relieve pressure.

2. The process of claim 1, further including:
   mixing a portion of the first composition with at least a portion of the second composition; and supplying the resulting mixture to the forming manifold so that the extruded plurality of flows from the forming manifold exhibit striations.

3. The process of claim 2, wherein the mixing step includes use of a static mixer to effect intermixing of the portion of the first composition and the portion of the second composition.

4. The process of claim 1, wherein the step of supplying a first composition under pressure includes extruding the first composition.

5. The process of claim 1, wherein the step of supplying a first composition under pressure is effected using a cooking extruder.

6. The process of claim 1, wherein the step of supplying a first composition under pressure is effected using a twin-screw feeder.

7. The process of claim 1, wherein the step of supplying the first composition under pressure includes pumping the first composition.

8. The process of claim 1, wherein the step of supplying a second composition under pressure includes extruding the second composition.

9. The process of claim 1, wherein the step of supplying a second composition under pressure is effected using a cooking extruder.

10. The process of claim 1, wherein the step of supplying a second composition under pressure is effected using a twin-screw feeder.

11. The process of claim 1, wherein the step of supplying a second composition under pressure includes pumping the second composition.

12. The process of claim 11, wherein the first time interval and the second time interval are unequal.

13. The process of claim 11, wherein the first time interval and the second time interval are equal.

14. The process of claim 1, wherein the step of dividing the first composition into a plurality of core streams is effected at least in part by branched internal passages of the forming manifold.

15. The process of claim 1, wherein the step of dividing the second composition into a plurality of flows is effected at least in part by branched internal passages of the forming manifold.

16. The process of claim 1, wherein the separating step severs the core stream between each adjacent pair of masses.

17. The process of claim 1, wherein the severing step is performed by an ultrasonic blade.

18. The process of claim 1, wherein the separating step severs the core streams such that at least two masses are connected with a continuous core.

19. The process of claim 1, wherein the shaping step includes forming at least one flow to encase the lateral surface of at least two core streams.

20. The process of claim 1, further including modulating each of the plurality of flows.

21. A process for making a food product having an inner component and an outer component, consisting essentially of the steps of:
  supplying a first composition under pressure to a forming manifold;
  supplying a second composition under pressure to the forming manifold;
  dividing the first composition into a plurality of core streams using the forming manifold;
  dividing the second composition into a corresponding plurality of flows using the forming manifold;
  extruding the core streams through corresponding orifices of the forming manifold, each core stream having a lateral surface shaped by the corresponding orifice;
  shaping each of the plurality of flows to substantially encase the lateral surface of the core stream;
  extruding the plurality of flows through forming surfaces of the forming manifold;
  intermittently interrupting the plurality of flows while extrusion of the core streams continues so as to obtain continuous cores with a plurality of masses spaced longitudinally therealong and so as to control dribbling;
  separating the core streams between adjacent ones of the plurality of masses to obtain food products without further molding or shaping,
  wherein the step of intermittently interrupting the plurality of flows:
  stops the plurality of flows for a first time interval;
  permits the plurality of flows to discharge from the forming manifold for a second time interval; and
  sequentially repeats the stopping and permitting steps; and
  wherein the step of intermittently interrupting the plurality of flows further includes cyclically moving a pair of gates between a first position where the gates abut and occlude the plurality of flows from being discharged from the forming manifold and a second position where the gates are spaced from one another and simultaneously permit the extruding of the plurality of flows onto the plurality of core streams wherein the step of intermittently interrupting the plurality of flows further includes operating a first valve to stop flow of the second composition to the forming manifold so as to relieve pressure.

* * * * *